United States Patent
Takamatsu et al.

(10) Patent No.: US 6,283,937 B1
(45) Date of Patent: Sep. 4, 2001

(54) IRRIGATION/ASPIRATION APPARATUS

(75) Inventors: Yuichi Takamatsu, Kariya; Kiyoshi Makihara, Gamagori, both of (JP)

(73) Assignee: Nidek Co. Ltd., Aichi (JP)

( * ) Notice: Subject to any disclaimer, the term of this patent is extended or adjusted under 35 U.S.C. 154(b) by 0 days.

(21) Appl. No.: 09/342,598

(22) Filed: Jun. 29, 1999

(30) Foreign Application Priority Data

Jun. 30, 1998 (JP) .................................. 10-184975

(51) Int. Cl.⁷ .................................................. A61M 1/00
(52) U.S. Cl. .................................................. 604/31
(58) Field of Search ................... 604/27, 30, 31, 604/35, 118, 119, 122, 22, 43, 45, 48, 65, 66, 67, 93.01; 606/107, 166; 417/540

(56) References Cited

U.S. PATENT DOCUMENTS

| | | | |
|---|---|---|---|
| 2,474,512 | * 6/1949 | Bechtold et al. | |
| 3,693,613 | * 9/1972 | Kelman | 128/24 A |
| 3,902,495 | * 9/1975 | Weiss et al. | 128/276 |
| 4,650,462 | 3/1987 | DeSatnick et al. | 604/30 |
| 4,718,895 | 1/1988 | Kurtz et al. | 604/119 |
| 4,921,477 | * 5/1990 | Davis | |
| 5,520,638 | 5/1996 | O'Quinn et al. | 604/67 |
| 5,693,013 | * 12/1997 | Geuder | |
| 5,810,765 | 9/1998 | Oda | 604/31 |
| 6,149,621 | * 11/2000 | Makihara | 604/27 |

FOREIGN PATENT DOCUMENTS

| | | |
|---|---|---|
| 0 494 089 A1 | 7/1992 | (EP) |
| 2-504593 | 12/1990 | (JP) |
| 8-10281 | 1/1996 | (JP) |
| WO 89/03230 | 4/1989 | (WO) |

* cited by examiner

*Primary Examiner*—Sharon Kennedy
*Assistant Examiner*—Catherine Serke
(74) *Attorney, Agent, or Firm*—Finnegan, Henderson, Farabow, Garrett & Dunner, L.L.P.

(57) ABSTRACT

An irrigation/aspiration apparatus for aspirating and discharging drainage from a surgical site by a surgical device to which an aspiration tube is being connected, the apparatus comprising, a suction pump which produces suction pressure through the aspiration tube, a chamber provided between the surgical device and the suction pump in communication with the aspiration tube, and an expansible and contractible gaseous-filed bag which is filled with gas and provided within the chamber.

7 Claims, 5 Drawing Sheets

| | PERFORMANCE OF THE APPARATUS | CLOSURE | SUCTION PRESSURE RANGE | PULSATION DAMPING |
|---|---|---|---|---|
| ① | IRRIGATION | | + 70 ~ 0 mmHg | NOT NECESSARY |
| ② | IRRIGATION + ASPIRATION | NOT CLOSED | 0 ~ -120 mmHg | NECESSARY |
| ③ | IRRIGATION + ASPIRATION | CLOSED | 0 ~ -500 mmHg | NOT NECESSARY |
| ④ | REFLUX | | +100 ~ 0 mmHg | NOT NECESSARY |

PRIOR ART

IRRIGATION/ASPIRATION APPARATUS

BACKGROUND OF THE INVENTION

1. Field of the Invention

The present invention relates to an irrigation/aspiration apparatus which supplies an irrigation fluid to a surgical site and aspirates the irrigation fluid therefrom with residual tissue. More specifically, the present invention relates to a mechanism which is advantageous to damp out or absorb pulsations caused by a peristaltic suction pump.

2. Description of Related Art

One conventionally known irrigation/aspiration apparatus supplies an irrigation fluid through an irrigation tube into a surgical site and removes the irrigation fluid and residual tissue therefrom by suction. In the field of ophthalmology, this kind of apparatus is used, for example, in cataract surgery, vitreous surgery and the like. The apparatus is generally provided with a peristaltic pump as a pump for effecting suction of the residual tissue. The peristaltic pump, however, causes pulsations which result in the disadvantage that the suction pressure varies.

Figure 7:
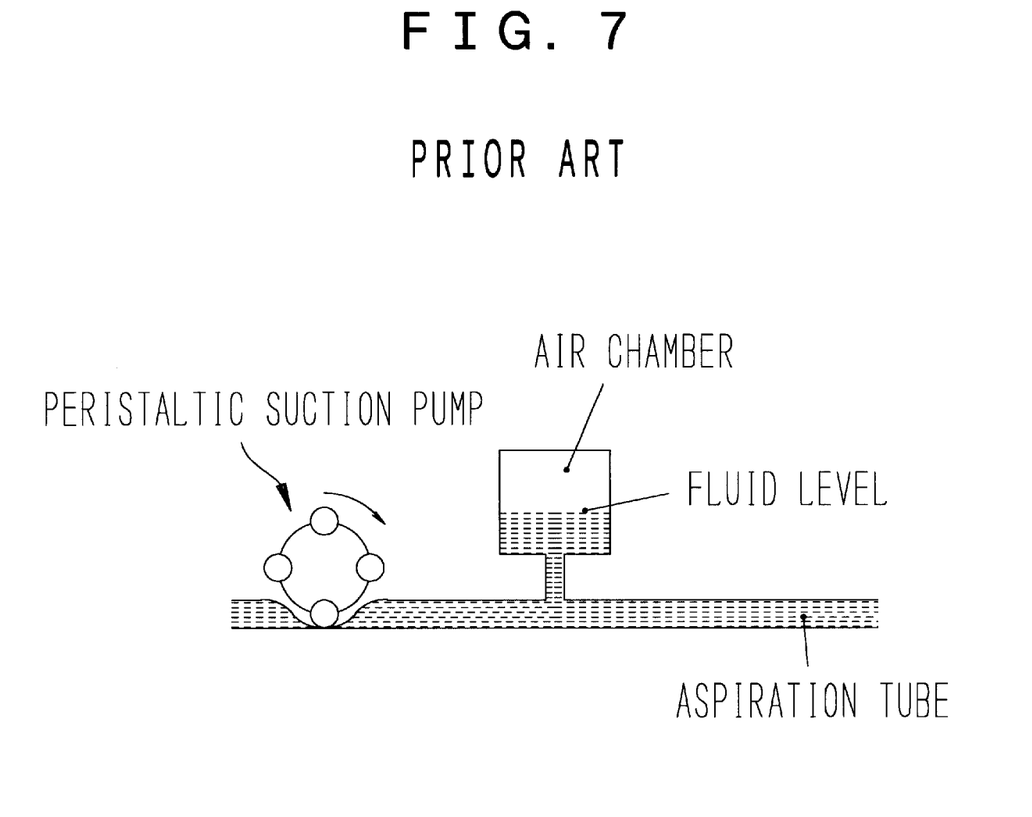
FIG. 7 is a view showing a configuration of a conventional type pulsation damping portion.

One known arrangement to address the above disadvantage is, as shown in FIG. 7, to provide an air chamber in which air is sealed in the vicinity of the peristaltic pump. The air sealed in the air chamber expands and contracts in response to change in the suction pressure, thereby to accomplish rising and falling movements of a fluid level. As a consequence, the pulsations are dammed out and controlled.

With such a configuration, however, when the suction pressure through the aspiration tube becomes high (becomes more negative), the air in the air chamber may leak into the aspiration tube, which raises a possibility of change in the amount of the air. This presents a problem that the pulsation damping may not be constant. In addition, the unlimited expansion and contraction in response to the suction pressure presents another problem that rising of the suction pressure (response to the suction) may be slow.

SUMMARY OF THE INVENTION

The present invention has been made in view of the above circumstances and has an object to overcome the above problems and to provide an irrigation/aspiration apparatus which is excellent in response to the suction pressure and capable of stable damping of the pulsations.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an irrigation/aspiration apparatus for aspirating and discharging drainage from a surgical site by a surgical device to which an aspiration tube is being connected, the apparatus of this present invention comprises a suction pump which produces suction pressure through the aspiration tube, a chamber provided between the surgical device and the suction pump in communication with the aspiration tube, and an expansible and contractible gaseous-filed bag which is filled with gaseous and provided within the chamber.

According to the present invention, the pulsations caused by the peristaltic suction pump can be reduced, and therefore, excellent response to the suction pressure can be achieved at high suction pressure. In addition, abrupt change in the pressure within the surgical site may be controlled as well.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
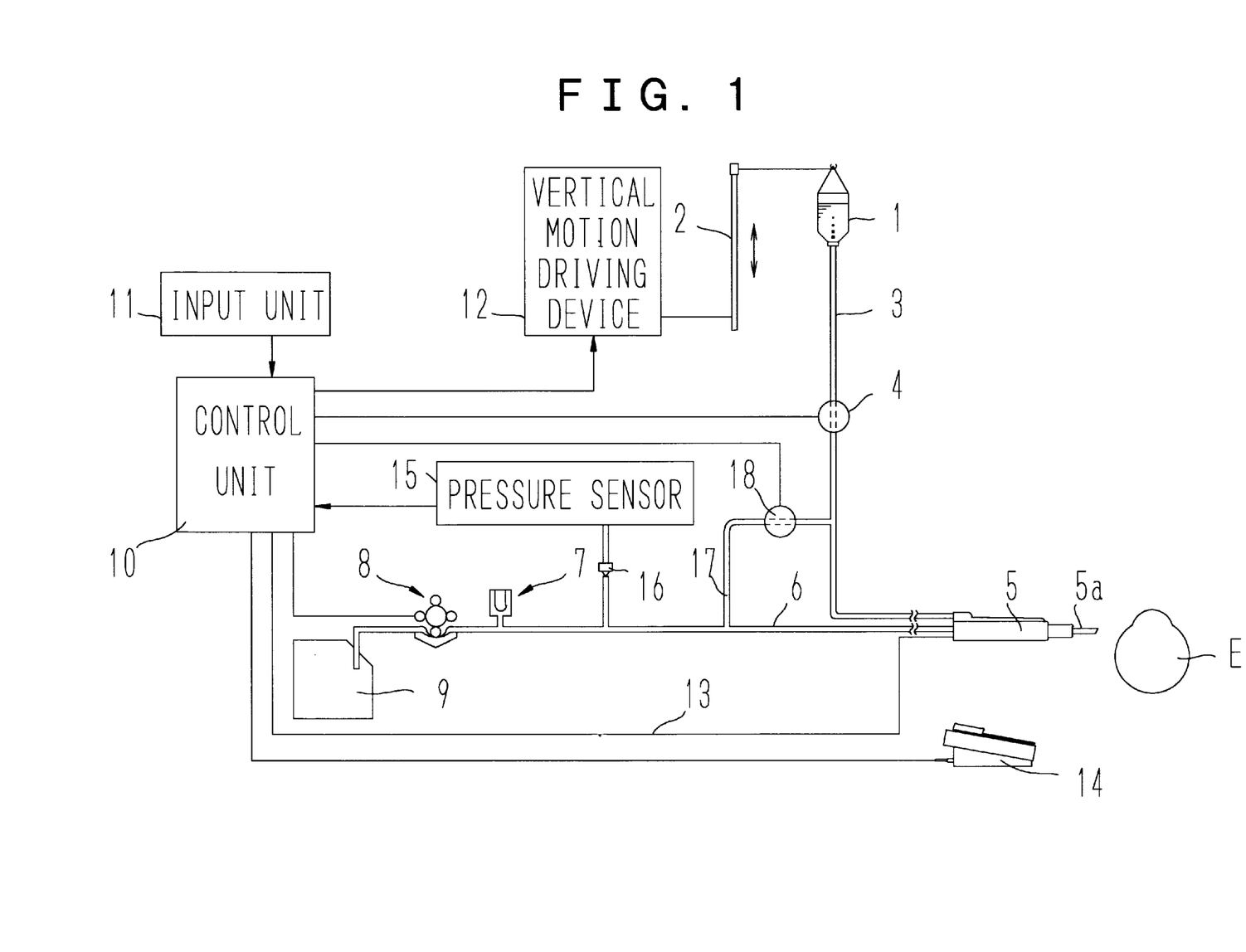
FIG. 1 is a view showing a schematic configuration of an irrigation/aspiration apparatus embodying the present invention.

A detailed description of one preferred embodiment of an irrigation/aspiration apparatus for performing surgery on a patient's eye having cataract embodying the present invention will now be given referring to the accompanying drawings. FIG. 1 is a view showing a schematic configuration of the irrigation/aspiration apparatus of the present invention. It should be noted that, in the descriptions, "suction pressure increases (suction pressure rises)" means that the suction pressure becomes more negative and "suction pressure decreases (suction pressure drops)" means that the suction pressure becomes closer to positive.

An irrigation bottle 1 filled with an irrigation fluid is suspended from an irrigation pole 2. A control unit 10 drives and controls a vertical motion driving device 12 so as to vertically move the pole 2 to a height set with the use of an input unit 11. The bottle 1 is adjusted its height by the vertical motion of the pole 2 thereby to regulate pressure of the irrigation fluid.

The irrigation fluid from the bottle 1 is supplied through an irrigation tube 3 to a surgical handpiece 5 being held in a surgeon's hand, thereby to be injected into a patient's eye E. The irrigation tube 3 is provided with a control valve 4 at an intermediate point thereof. The control unit 10 controls opening and closing of the valve 4 so that the flow of the irrigation fluid is regulated. In this embodiment, the handpiece 5 is a US handpiece, which emulsify an opaque crystalline lens with a crushing tip $5a$ provided at an end thereof by ultrasonic vibrations and remove the emulsified particles by suction. The ultrasonic vibrations of the tip $5a$ are produced by supplying electric power to an ultrasonic vibrator provided within the handpiece 5 via a power supply cable 13.

Connected to the handpiece 5 is an aspiration tube 6 having flexibility. Intermediately of its ends, the aspiration tube 6 is provided with a connecting portion 16, which connects with a pressure sensor 15, and a peristaltic suction pump 8. The aspiration tube 6 is in communication with the irrigation tube 3 via a bypass tube 17 and the fluid flow through the bypass tube 17 is controlled by a control valve 18. That is to say, the pressure sensor 15 detects the suction pressure at all times. When the suction pressure rises higher than a preset value, the valve 18 opens as necessary under the control by the control unit 10 to permit the irrigation fluid to flow from the irrigation tube 3 into the aspiration tube 6 via the bypass tube 18 so as to decrease the suction pressure. The upper limit of the suction pressure is set by operating switches of the input unit 11.

The pump 8 is rotatably driven and controlled by the control unit 10 in response to a signal indicative of a foot position where a foot switch 14 is depressed. The rotation applies the suction pressure through the aspiration tube 6 so that the irrigation fluid and the residual tissue are sucked out from the handpiece 5 and discharged into a drainage bag 9.

Figure 2:
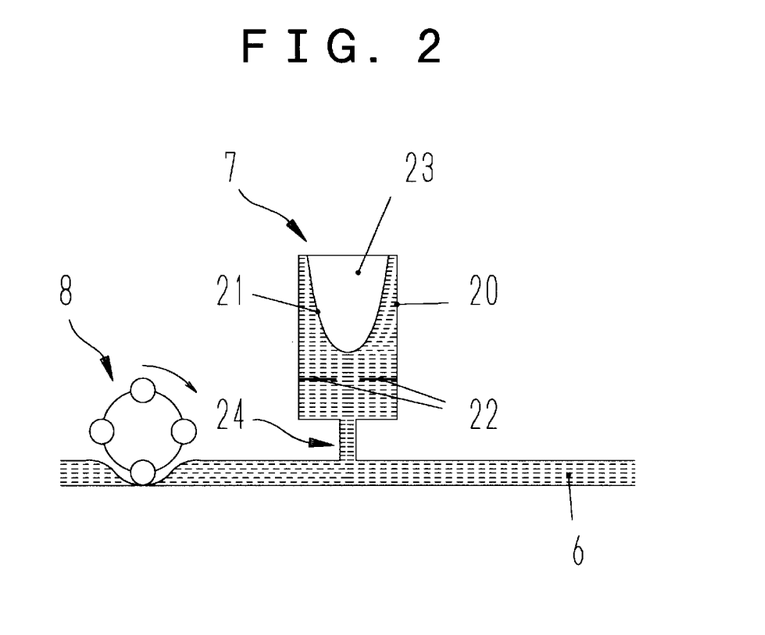
FIG. 2 is a view showing a configuration of a pulsation damping portion provided in the irrigation/aspiration apparatus shown in FIG. 1.

Provided between the handpiece 5 and the pump 8 is a pulsation damping portion 7. FIG. 2 is a view showing a schematic configuration of this damping portion 7. The damping portion 7 comprises a chamber 20 in communication with the aspiration tube 6 via a communicating portion 24, an expansible and contractible balloon 21 provided in the chamber 20, and a limiting portion (limiting plate) 22 for limiting deformation of the balloon 21. The balloon 21 is mouthed, like a dome, to the chamber 20 at the upper wall (on an opposed side to the communicating portion 24) thereof. A sealed space formed between the upper wall of the chamber 20 and the balloon 21 is an air chamber 23 containing air therein.

Upon rotatably driving the pump 8, the suction pressure is applied to the aspiration tube 6. As the suction pressure increases, the balloon 21 (the air chamber 23) expands. The expansion or contraction of the balloon 21 (the change in the capacity of the air chamber 23) in response to the suction pressure change permits to attenuate and control the suction pressure change caused by pulsations.

Figure 3:
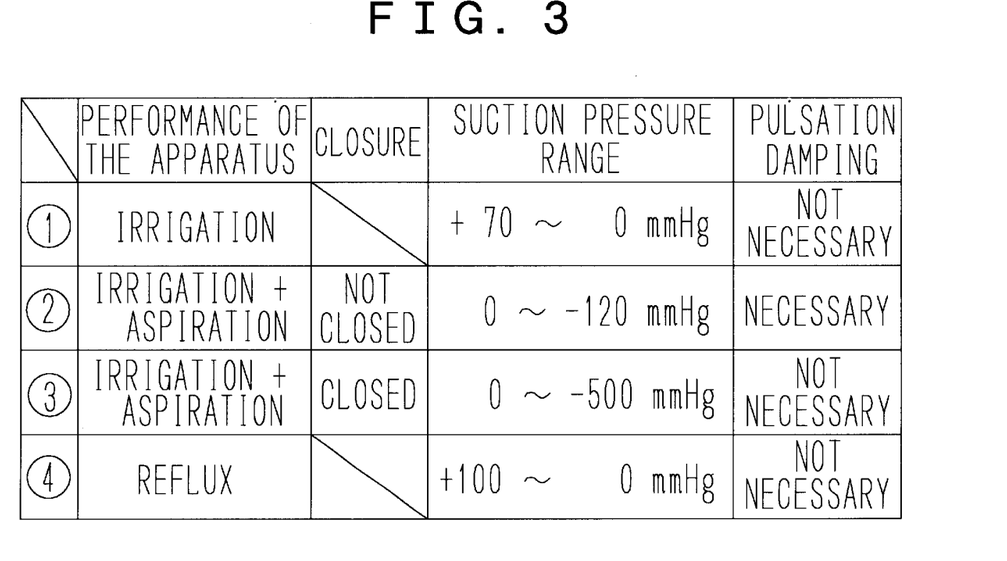
FIG. 3 is a table showing relations between suction pressure and pulsation damping.

In addition, with the limiting portion 22 arranged at a suitable position with respect to the expansion of the balloon 21, the function of damping and controlling the pulsations is stopped from working at the suction pressure which is equal to or higher a preset value (more negative than the preset value). Hereinafter, description is given regarding the position suitable for provision of the limiting portion 22 with reference to FIG. 3. FIG. 3 is a view showing relations between the range of the suction pressure and necessity of the pulsation damping upon performing irrigation/aspiration in simulated surgery.

Upon incising the patient's eye at an initial stage of the surgery, for example, only supply of the irrigation fluid is performed without driving the pump 8 (the case ① shown in FIG. 3). In this case, as there are no pulsations, there is no need for pulsation damping either.

In the case of inserting the tip 5a provided at the end of the handpiece 5 into the eye E to crush and emulsify the opaque lens nucleus and to remove the lens particles with the irrigation fluid (the case ② shown in FIG. 3), driving of the pump 8 causes pulsations. In response to the pulsations, the crystalline lens and the iris may move, or other influences may be exerted on the eye E. Consequently, the function of pulsation damping needs to be effected. The range of the suction pressure change in which the function of pulsation damping is necessary should be sufficiently within the range 0 to −120 mmHg, according to the simulation (the range may vary in relation to the inner diameter of the aspiration tube or of the crushing tip). Therefore, within this range, the balloon 21 is made to expand or contract in response to the suction pressure change.

To keep the crystalline lens or the like during the surgery, the tip 5a is closed at the end with the crystalline lens nucleus or the like (the case ③ shown in the FIG. 3), involving further increase in the suction pressure. Closing of the tip 5a causes abrupt shift of the pressure through the aspiration tube 6 toward more negative. Yet, since the tip 5a is closed at the end, the eye E is not affected despite the suction pressure change in response to the pulsations caused by the pump 8. In this case, the function of pulsation damping does not have to be effected.

However, in case that the balloon 21 unlimitedly expands due to a great amount of negative pressure, the closure may be suddenly released (the clogging crystalline lens or the like is sucked out). In response to this abrupt change in the suction pressure, the balloon 21 will also contract instantly. When the balloon 21 abruptly returns to its original size, the irrigation fluid in the eye E is abruptly sucked, raising a possibility that the anterior chamber of the eye E withers. The larger the amount of difference between expansion and contraction is, the larger the influence exerted on the anterior chamber will be.

To address the above-situation, the limiting portion 22 is arranged in a position allowing the balloon 21 to expand until the suction pressure reaches the maximum (−120 mmHg) requiring the function of pulsation damping, but prohibiting to expand any further (the function of pulsation damping is allowed to work only within the range of 0 to −120 mmg as shown in the case ②, but prohibited from working when the suction pressure becomes more negative). Because of this arrangement, the difference in a balloon shape upon returning to the original size is kept small so as to lessen the amount of drainage sucked at the moment the closure is released. Consequently, withering of the anterior chamber (surge) can be restricted.

Figure 4:
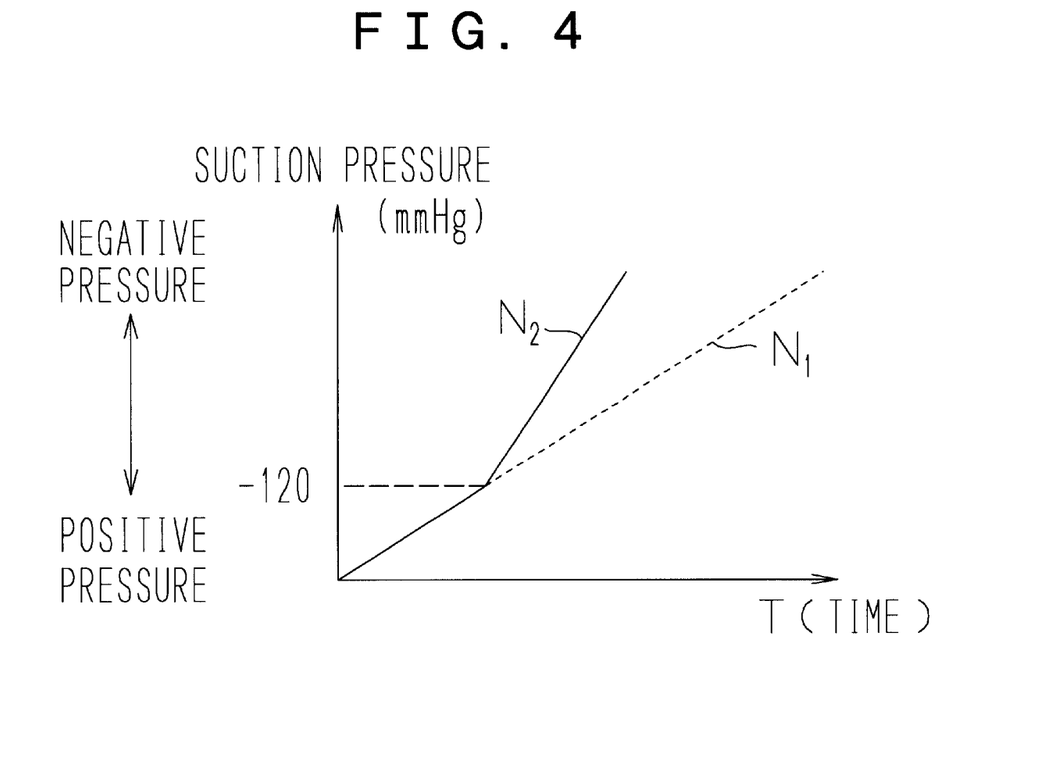
FIG. 4 is a chart showing curves which represent change in the suction pressure.

In addition, by limiting the expansion of the balloon 21 with the limiting portion 22, at the pressure higher (more negative) than the maximum which requires the function of pulsation damping, less influence is exerted by the expansion of the balloon 21 on the suction response (raising of the suction). Accordingly, comparatively quick suction response can be achieved. As shown in FIG. 4, in comparison to the curve N1 that represents the change in the suction pressure without the limitation, the change in the suction pressure with the limitation that prohibits the function of pulsation damping after the suction pressure exceeds −120 mmHg is represented by the curve N2. The curve N2 indicates greater change in the suction pressure versus time and quicker response to the suction pressure. The difference is bigger especially at the high suction pressure, and as apparent from that, limiting the expansion is effective at the high suction pressure.

As described above, by appropriately setting the capacity the balloon 21 and the position that the limiting portion 22 functions, the pulsations can be dammed put only within an intended range of the suction pressure. Therefore, even surgery with the use of high suction pressure can be carried out without loss of the response to the suction pressure.

The reflux function which temporarily reverses the pump 8 is effected (a switch therefor is included in the foot switch 14) to release the edge of the tip, in other words the closure, or the like. As it is not used with the closure released, the pulsation damping is not necessary (the case ④ in FIG. 3).

So far, one preferred embodiment has been described. Hereinafter, a modification of the damping portion 7 will be described with reference to FIG. 5. In the figure, the same reference numbers as in the previous embodiment indicate similar components.

Figure 5:
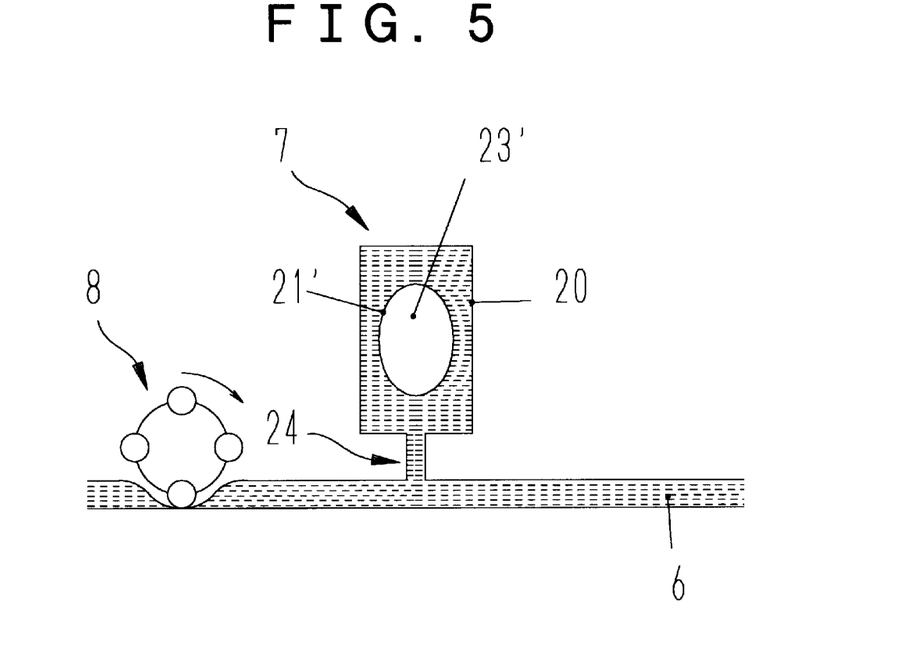
FIG. 5 is a view showing a configuration of a modified pulsation damping portion.

The chamber 20 is provided in communication with the aspiration tube 6 via the communicating portion 24. A balloon 21' is provided, without being fixed, in the chamber 20 filled with an aspiration fluid. The internal surface of the balloon 21' forms an air chamber 23' having air sealed therein. The balloon 21' expands and contracts in response to the suction pressure change thereby to damp out and control the pulsations in a like manner as the previous embodiment.

In this embodiment, in addition, the camber 20 is relatively larger with respect to the communicating portion 24. This setting prohibits the balloon 21' from expanding more than the capacity of the chamber 20. Provision of the chamber 20 in capacity appropriate in relation to the volume of the balloon 21' being expanded will have the same function as that of the limiting portion (limiting plate) in the previous embodiment.

In the above descriptions, the expansion is limited through the use of the limiting plate in the former embodiment and with the capacity of the chamber in the latter embodiment. However, it is surely possible to make use of the capacity of the chamber in the former embodiment and the limiting plate in the latter embodiment.

Figure 6A:
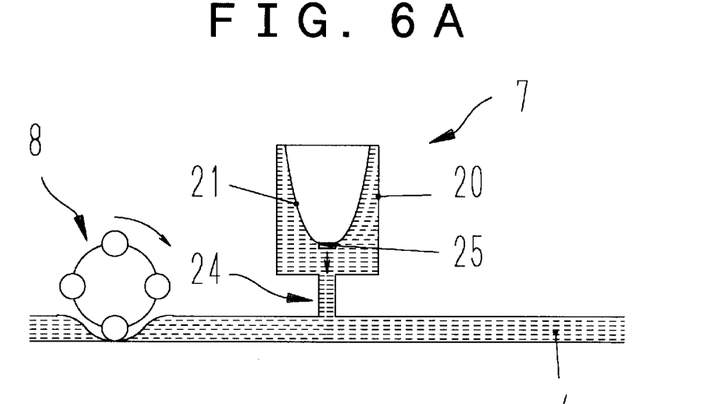
FIGS. 6A, 6B and 6C are views showing configurations of modified pulsation damping portions.
Figure 6B:
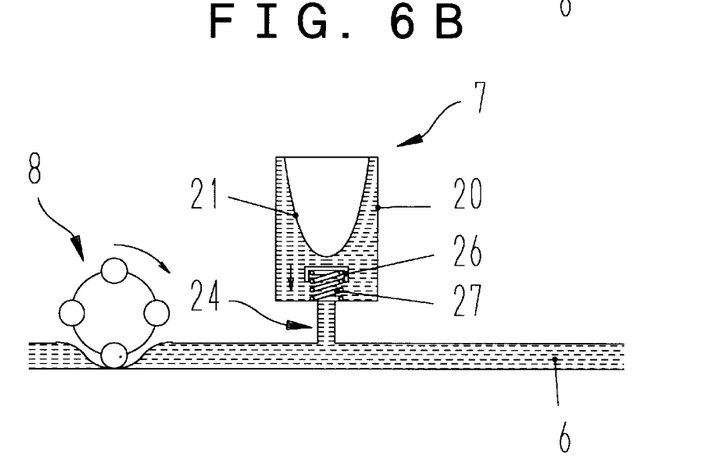
Figure 6C:
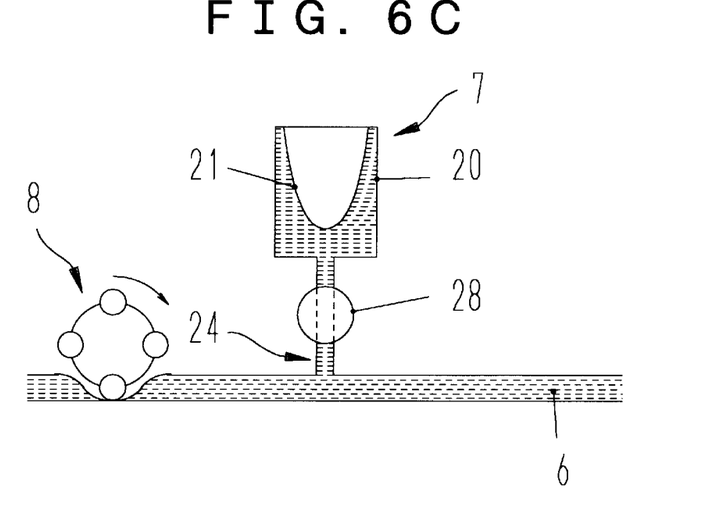

Further, various modifications for limiting the balloon expansion will be mentioned with reference to FIGS. 6A–6C. In the embodiment shown in FIG. 6A, the balloon 21 is provided with a closing plug 25 at the end thereof for closing the communicating portion 24. The balloon 21 expands in response to the suction pressure through the aspiration tube 6 and when the preset suction pressure is reached, the closing plug 25 closes the communicating portion 24. The closure of the communicating portion 24 disconnects the balloon 21 from the aspiration tube 6. As a result, effect upon the balloon 21 has nothing to do with the aspiration tube 6. Also, after the closure of the communicating portion 24, the pressure in the chamber 20 remains unchanged, and therefore, the balloon 21 does not expand any further.

In the embodiment shown in FIG. 6B, the communicating portion 24 is provided with a closing valve 26 for closing the communicating portion 24 and the closing valve is provided with a spring 27. When the preset suction pressure is applied, preponderance of the suction pressure over the energization of the spring 27 makes the closing valve 26 close the communicating portion 24. It is also possible to make the balloon 21, as it expands, press down the closing valve 26 thereby to close the communicating portion 24. After the closure has been made, the same effect as in the FIG. 6A can be obtained.

In the embodiment shown in FIG. 6C, the communicating portion 24 is provided with a control valve 28 for effecting opening and closing of the communicating portion 24. The control valve 28 is driven and controlled by the control unit 10. When the suction pressure detected by the sensor 15 reaches the preset suction pressure, the control unit 10 controls the control valve 28 to execute opening or closing operation. By closing the communication portion 24, when the suction pressure becomes equal to, or higher than, the preset pressure, the same effect as in the FIGS. 6A and 6B can be obtained. In the case of this embodiment, the preset suction pressure is input from the input unit 11 and the preset pressure may be changed by the surgeon arbitrarily based on surgical operations to be performed.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An irrigation/aspiration apparatus for aspirating and discharging drainage inside an eye to be examined with a handpiece to which an aspiration tube is connected, the apparatus comprising:

a peristaltic suction pump which produces suction pressure through the aspiration tube;

a sensor which detects the suction pressure inside the aspiration tube;

a suction pressure reducing means for reducing the suction pressure when the suction pressure detected by the sensor is above a preset value;

a chamber having one end in communication solely with the aspiration tube, said communication occurring between the handpiece and the peristaltic suction pump, and said chamber being hermetically closed off from atmosphere;

a bag filled with gas disposed inside the chamber, said bag having a portion made of an expansible and contractible material; and a limiter which limits expansion of the bag within a preset range when the aspiration tube is closed so that withering of an anterior chamber of the eye is prevented.

2. The irrigation/aspiration apparatus according to claim 1, wherein the limiter includes a limiting plate disposed inside the chamber for restricting the expansion of the bag.

3. The irrigation/aspiration apparatus according to claim 1, wherein the bag is balloon-like.

4. An irrigation/aspiration apparatus for aspirating and discharging drainage inside an eye to be examined with a handpiece to which an aspirator tube is connected, the apparatus comprising:

a peristaltic suction pump which produces suction pressure through the aspiration tube;

a sensor which detects the suction pressure inside the aspiration tube;

a suction pressure reducing means for reducing the suction pressure when the suction pressure detected by the sensor is above a preset value;

a chamber having one end in communication solely with the aspiration tube, said communication occurring between the handpiece and the peristaltic suction pump, and said chamber being hermetically closed off from atmosphere;

bag filled with gas disposed inside the chamber, said bag having a portion made of an expansible and contractible material; and a limiter which limits expansion of the bag within a preset range when the aspiration tube is closed so that withering of an anterior chamber of the eye is prevented;

wherein the limiter includes closure means for prohibiting drainage from flowing into and out of an interior of the chamber based on the suction pressure detected by the sensor.

5. The irrigation/aspiration apparatus according to claim 4, wherein the bag is balloon-like.

6. An irrigation/aspiration apparatus for aspirating and discharging drainage inside an eye to be examined with a handpiece to which an aspirator tube is connected, the apparatus comprising:

a peristaltic suction pump which produces suction pressure through the aspiration tube;

a sensor which detects the suction pressure inside the aspiration tube;

a suction pressure reducing means for reducing the suction pressure when the suction pressure detected by the sensor is above a preset value;

a chamber having one end in communication solely with the aspiration tube, said communication occurring between the handpiece and the peristaltic suction pump, and said chamber being hermetically closed off from atmosphere;

a bag filled with gas disposed inside the chamber, said bag having a portion made of an expansible and contractible material; and limiter which limits expansion of the bag within a preset range when the aspiration tube is closed so that withering of an anterior chamber of the eye is prevented;

wherein the limiter includes a closing plug mounted to the bag, which closes off a communication hole connected to the aspiration tube when the bag expands to a predetermined size.

7. The irrigation/aspiration apparatus according to claim 6, wherein the bag is balloon-like.

* * * * *

UNITED STATES PATENT AND TRADEMARK OFFICE
CERTIFICATE OF CORRECTION

PATENT NO. : 6,283,937 B1    Page 1 of 1
DATED : September 4, 2001
INVENTOR(S) : Yuichi Takamatsu et al.

It is certified that error appears in the above-identified patent and that said Letters Patent is hereby corrected as shown below:

Title page,
Item [57], ABSTRACT, line 8, "gaseous-filed" should read -- gaseous-filled --.

Column 6, claim 4,
Line 62, before "bag filled", insert -- a --.

Column 8, claim 6,
Line 8, before "limiter which limits", insert -- a --.

Signed and Sealed this

Fifth Day of March, 2002

*Attest:*

JAMES E. ROGAN
*Attesting Officer*     *Director of the United States Patent and Trademark Office*